United States Patent [19]

Okasinski

[11] Patent Number: 4,970,155

[45] Date of Patent: Nov. 13, 1990

[54] HSV HELPER VIRUS INDEPENDENT VECTOR

[75] Inventor: Gregory F. Okasinski, Zion, Ill.

[73] Assignee: Abbott Laboratories, Abbott Park, Ill.

[21] Appl. No.: 277,458

[22] Filed: Nov. 23, 1988

Related U.S. Application Data

[63] Continuation of Ser. No. 751,473, Jul. 3, 1985, abandoned, which is a continuation of Ser. No. 472,919, Mar. 7, 1983, abandoned.

[51] Int. Cl.$^5$ .................... C12N 5/10; C12N 7/01; C12N 15/38; C12N 15/86
[52] U.S. Cl. .................... 435/172.3; 435/69.1; 435/320; 435/240.2; 935/29; 935/32; 935/34; 935/70
[58] Field of Search .............. 435/172.3, 68, 320, 435/240.2; 935/29, 32, 33, 34, 55, 70

[56] References Cited

FOREIGN PATENT DOCUMENTS 0022685  1/1981  European Pat. Off. ............ 435/172

OTHER PUBLICATIONS

Stow, N. et al. in *Eukaryotic Expression Vectors* (ed Y. Gluzman), Cold Spring Harbor Laboratory, pp. 199–204, 1982.
Stow, N., *The Embo Journal*, vol. 1, No. 7, pp. 863–867, 1982.
Dubois, M., et al, *Proc. Natl. Acad Sci*, vol. 77, No. 8, pp. 4549–4553, 1980.
Burrell, C. J. et al., Nature, vol. 279, pp. 43–47, 1979.
Enquist, L. et al., *Gene*, vol. 7, pp. 335–342, 1979.
Post, Leonard E., et al., "A Generalized Technique for Deletion of Specific Genes in Large Genomes: αGene 22 of Herpes Simplex Virus 1 is Not Essential for Growth," CELL, vol. 25, 227–232, Jul. 1981.

*Primary Examiner*—Robin L. Teskin
*Assistant Examiner*—S. Nolan
*Attorney, Agent, or Firm*—Roberta L. Hastreiter

[57] ABSTRACT

This invention encompasses an eukaryotic expression vector constructed from a prokaryotic plasmid by inserting into the prokaryotic plasmid a mediator sequence and a promoter/regulatory sequence with a restriction endonuclease site for inserting a gene to be expressed. The gene to be expressed is inserted into the restriction endonuclease site in the promoter/regulatory sequence and the resulting plasmid is in turn used to transform a eukaryotic cell. The gene is expressed with or without viral mediation.

4 Claims, 1 Drawing Sheet

HSV HELPER VIRUS INDEPENDENT VECTOR

This application is a continuation of application Ser. No. 751,473, filed July 3, 1985, which is now abandoned. Applicants are claiming the benefit of the July 3, 1985, effective filing date of Application No. 751,473, under 35 U.S.C. §120 and which is a continuation of application Ser. No. 472,919, filed Mar. 7, 1983, which is also now abandoned.

BACKGROUND OF THE INVENTION

Figure 1:
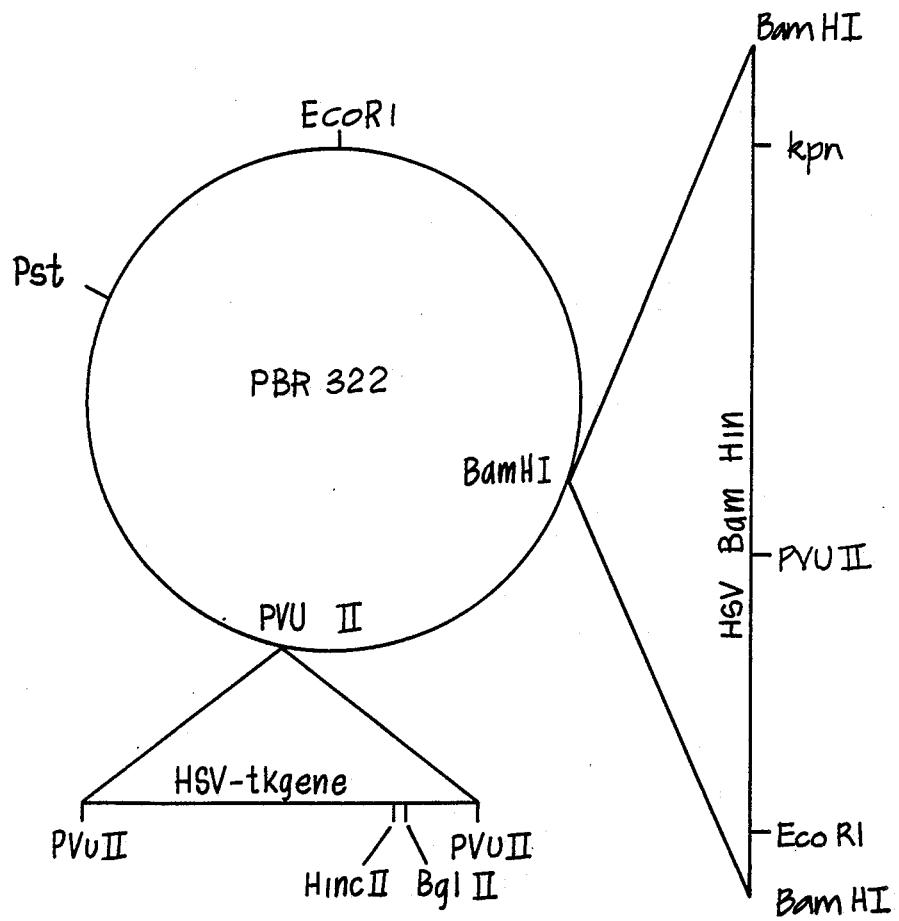
FIG. 1 is a schematic drawing of a prokaryotic plasmid with a viral mediator sequence and a promoter/regulatory sequence inserted therein.

Exogenous DNA has been expressed in higher eukaryotic cells by a variety of methods, principally as either a defective virus vector or by direct introduction of DNA containing a selectable marker. Defective virus vectors consist of exogenous DNA linked to a subset of viral genes, typically containing at least a viral origin of replication and a portion of the structural protein coding information of the virus. These vectors are introduced into eukaryotic cells and rescued with a helper virus. The resulting mixture of virus contains both defective viruses, linked to exogenous DNA, and helper virus. Defective SV-40 vectors are the best examples of current defective virus vectors. A variety of exogenous DNAs have been expressed in SV-40 derived vectors—Goff, SP. and Berg, P. Cell 9, 695–705 (1976), Hamer, Kaehler and Leder, P. 1980. Cell 21, 697–708 (1980); Mulligan, R.C., Howard, B.H. and Berg, P. Nature 277, 108–114 (1979); Gruss, P. and Khoury, G. Proc. Nat. Acad. Sci. USA 78, 133–137 (1981); Sveda, M.M. and Lai, C.J. Proc. Nat. Acad. Sci. USA 78, 5488–5492 (1981); and White, R.T., Berg, P. and Villarreal, L.P. J. Virol, 42, 262–274 (1981).

Alternately DNA is directly inserted into eukaryotic cells, by either calcium phosphate precipitation, Graham, F.L., and Van der Eb., A.J. Virology 52; 456–467 (1973); DEAE-dextran, McCutchan, J.H., and Pagano, J.S. J. Natl. Cancer Inst. 41,351–357 (1968); microinjection, Capecchi, M.R. Cell 22, 479,488 (1980); and recently by entrapment in liposomes, Wong, T.K., Nicolau, C., and Hofschneider, P.H. Gene 10, 87–94 (1980). Gene expression of exogenous DNA directly introduced into eukaryotic cells was initially achieved by transformation of thymidine kinase deficient (TK−) cells to a TK+phenotype by the herpes simplex virus (HSV) thymidine kinase gene, Bacchetti, S., and Graham, F.L. Proc. Natl Acad Sci. USA 74, 1590–1594 (1977); Maitland, N.J., and McDougall, J.K. Cell 11, 233–241 (1977; Wigler, M., Silverstein, S., Lee, L.S., Pellicer, A., Cheng, Y. and Axel, R., Cell 11, 223–232 (1977). Transformation of eukaryotic cells with exogenous DNA has also been reported for the adenine phosphoribosyl transferase gene, Lowy, I., Pellicer, A., Jackson, J.F., Sim, G.K., Silverstein, S., and Axel, R., Cell 22, 817–823 (1980); dihydrofolate reductase, O'Hare, K., Benoist, C., and Breathnach, R., Proc. Natl. Acad. Sci. USA 78, 1527–1531 (1981); various oncogenes, Cooper, G.M., Okenquist, S., and Silverman, L., Nature 284, 418–421 (1980); Shih, C., Shilo, B.Z., Goldfarb, M.P., Dannenberg, A., and Weinberg, R.A., Proc. Natl. Acad. Sci USA 76, 5714–5718 (1979); E. coli xanthine-guanine phosphoribosyl transferase, Mulligan, R.C. and Berg, P., Science 209, 1422–1427 (1980); and sequences coding for resistance to neomycin-kanamycin antibiotics, Southern, P.J., and Berg, P., J. Mol and App. Gen. 1, 327–341 (1982).

Recently, a herpes virus derived defective virus vector has been described by Spaete, R.R. and Frenkel, N., Cell 30, 295–304 (1982). This vector, like the SV-40 derived vectors, is propagated as a defective virus in an HSV population.

The cloning vector described in the present invention is a plasmid which is recognized in HSV infected eukaryotic cells as viral, allowing expression of exogenous DNA as though the sequences were HSV DNA. In addition, the vector is capable of directing expression in the absence of HSV infection.

BRIEF DESCRIPTION OF THE INVENTION

The general strategy for the construction of the eukaryotic expression vector is to insert a PvuII fragment containing the coding segments for the HSV tk gene into the pBR322 plasmid as a promoter/regulator sequence. The BamHI fragment from the F strain of HSV is then inserted as a viral mediator sequence into the resulting plasmid at the unique BamHI site. The gene to be expressed is inserted into a restriction endonuclease site on the PvuII fragment and the resulting plasmid is in turn used to transform an eukaryotic cell. The gene is expressed with or without viral mediation.

DETAILED DESCRIPTION OF THE INVENTION

This invention encompasses an eukaryotic expression vector constructed from a prokaryotic plasmid by inserting a viral mediator sequence contained in the BamHI N fragment of HSV DNA and a promoter/regulatory sequence with a restriction endonuclease site for inserting a gene to be expressed. The gene to be expressed is inserted in a restriction endonuclease site in the HSV promoter regulator sequence. Thus, the invention includes the eukaryotic expression vector, the eukaryotic expression vector with the gene inserted as well as the viral mediator DNA sequence which is contained in the BamHI N fragment of HSV-DNA. In a preferred embodiment, the prokaryotic plasmid is pBR322; the HSV promoter/regulatory sequence is a PvuII fragment of HSV DNA coding for the thymidinekinase gene and associated promoter/regulatory sequence with a restriction endonuclease site between the promoter and the initiator codon (the first adenine-thymidine-guanine (ATG) sequence) of the thymidine kinase gene, inserted in a PvuII site of the prokaryotic plasmid; and the HSV mediator sequence is the BamHI N fragment of HSV DNA inserted into a BamHI N site of the prokaryotic plasmid.

Those skilled in the genetic engineering arts will recognize a wide variety of genes such as genes for hepatitis A, B, core and Non A/Non B antigens which can be expressed by this expression vector.

The BamHI N fragment of HSV allows the maintenance of DNA sequences, contained within the expression vector, in eukaryotic cells. Inclusion of the BamHI N fragment into an eukaryotic expression vector permits the vector to be maintained as an extrachromosomal element within eukaryotic cells. The extrachromosomal state can be maintained for at least thirty cell generations, at low copy number, and thus the BamHI N fragment must contain an origin of replication recognizable by eukaryotic DNA polymerases. Thus the function of the BamHI N fragment is entirely independent of any function these sequences serve in HSV replication or gene expression.

A BamHI N fragment of HSV DNA is inserted in the BamHI site of the pBR322 plasmid as the HSV mediator sequence and a PvuII fragment of HSV DNA coding for the thymidine kinase gene is inserted into the PvuII site of the pBR322 plasmid as the promotor/regulatory sequence. A gene to be expressed, such as the gene for the hepatitis B virus surface antigen, is conveniently inserted into the BglII site in the PvuII insert. When baby hamster kidney cells are transformed with this later vector and infected with herpes simplex virus, hepatitis B surface (HBsAg) antigen is produced at a rate of $10^4$–$10^5$ molecules per cell.

When this expression vector and a selectable gene such as HSV thimidine kinase (tk) gene are introduced into mouse cells which are thymidine kinase negative (Ltk- cells), a cell line is established which is capable of gene expression (HBsAg) without virus.

The invention is illustrated by the hereinafter set out examples and the examples are not intended to limit the invention. Those skilled in the genetic engineering arts will recognize that DNA segments obtained from a viral source and used for the mediator sequence and the promoter sequence can be synthesized.

EXAMPLE 1

Restriction endonucleases were obtained from Bethesda Research Laboratories and New England Bio Labs—and digestions carried out by methods recommended by the manufacturer. T4 DNA ligase made from T4 infected *E. coli* was obtained from New England Bio Labs and calf alkaline phosphatase from Boehringer Mannheim.

The pBR322 plasmid is propagatged in *E. coli* HB101. The organism is grown in TYEG medium (101g/L tryptone, 5g/L yeast extract, 5g/l NaCl/lg/l D glucose) to a density of $A_{600}$ 0.8–0.9, chloramphenicol added to 150 mg/ml, and the culture incubated for an additional 12 hours at 37° C. while shaking. The cells are collected after centrifugation for 10 minutes at 5,000 rpm in a GSA rotor, resuspended with 50 ml of 15% sucrose in TE (10 mm Tris pH 7.8, 1M EDTA) and centrifuged again. The cell pellet is resuspended with 10–15 ml of 15% sucrose by weight in TE, lysozyme added to 2 mg/ml, and incubated on ice for 30 minutes. The cells are rapidly freeze-thawed in a dry ice methanol bath; EDTA, NaCl, and sodium dodecylsulfate (SDS) are added to 0.1 molar, 1.0 molar and 1% weight/volume respectively, and the lysate incubated overnight at 4° C. Chromosomal DNA is removed by centrifugation for 30 minutes at 25,000 rpm in an SW-27 rotor at 4° C. Solid cesium chloride (0.97 g/ml) and ethidium bromide (250 mg/ml) are added to the supernate, and the solution is centrifuged for 48 hours at 40,000 rpm in a Ti50 or Ti60 rotor at 20° C. The plasmid DNA is visualized by long wave UV light and removed by side puncture of the centrifuge tube. The plasmid DNA is extracted several times with cesium chloride saturated isopropanol, dialized against TE, concentrated by ethanol precipitation, resuspended in TE, and stored at 4° C. This procedure is used to prepare and purify all plasmid DNAs described herein.

A commercially available (Bethesda Research Laboratories) BamHI Q fragment of HSV (hereinafter referred to as pHVS 106) is purified as described above and digested with PvuII. The digested plasmid DNA is extracted with phenol: chloroform, ethanol precipitated, and resuspended in ligation buffer (50 mM Tris pH 7.8, 10 mM $MgCl_2$ 20 mM dithiothreitol (DTT), 1 mM adenosine triphosphate (ATP), 50 microgram/ml bovine serum albumin).

The pBR322 plasmid is similarly digested with PvuII, phenol: chloroform extracted, ethanol precipitated and resuspended in TE. The PvuII digested pBR322 DNA is incubated with calf alkaline phosphatase (CAP) at a concentration of 0.5 units CAP/microgram DNA for 30 minutes at 37° C. The phosphatased DNA is phenol: chloroform extracted, ethanol precipitated and resuspended in ligation buffer. This DNA is ligated with the PvuII digested HSV tk plasmid at a ratio of 1:1 with 10 units T4 DNA ligase/ul reaction mixture, for 16 hours at 16° C. The ligated DNA is diluted 1:1 with TCM (10 mM Tris pH 7.0, 10 mM $CaCl_2$ 10 mM $MgSO_4$) and used to transform calcium treated *E. coli* HB101. Transformed *E. coli* are selected in the presence of ampicillin (25 microgram/ml) and tetracycline (15 microgram/ml). Selected colonies are tested for the plasmid containing the promoter regulator sequence by preparation of quick plasmid DNA exactly as described by Birnboim and Doly (Birnboim, H.D., and Doly, J., Nucleic Acids Res. 7, 1513–1523 (1979)). The plasmid containing the promoter/regulatory sequence (referred to as pBHV tk2) is identified by the presence of a PvuII digest fragment containing single BglII, EcoRl, and Rpn restriction enzyme sites.

HSV-DNA is prepared from infected Hep-2 cells (a continuous human cell line established from epidermoid carcinoma tissue from the larynx) by sodium-iodide density gradient centrifugation of Hep-2 cell lysates in the presence of ethidium bromide (Walboomers, J.M.M. and Ter Schegget, J., Virology 74, 256–258 (1976)). The viral DNA (1.0 ug) is digested with BamHI and ligated to BamHI digested pBR322 (0.1 ug) at a concentration of 100 ug/ml with 1 unit ligase/ul reaction at 16° C. for 3 hours, diluted 1:5 with ligation buffer and the ligation continued for an additional 15 hours. The ligated DNA is diluted 1:1 with TCM and used to transform calcium treated *E. coli*. Ampicillin resistant tetracycline sensitive colonies are isolated and screened for HSV-DNA inserts by the method of Birnboim and Doly. This plasmid is identified by electrophoretic co-migration of BamHI N fragments from BamHI digests of plasid DNA and HSV-DNA. The presence of the HSV-BamHI N fragment was confirmed by identification of internal ECORI, PvuII, and KpnIsites (Post, L.E., Conley, A.J., Mocarski, E.S., and Roizman, B. Proc. Natl. Acad. Sci. 77, 4201–4205 (1980), Locker, H. and Frenkel, N., J. Virol. 32, 429–441 (1979)). The plasmid was propagated in *E. coli* HB101 and purified by cesium chloride-ethidium bromide density centrifugation as described above. This plasmid is referred to as pBHVn.

Construction of Eukaryotic Expression Vector

The pBHVtk2 plasmid with the promoter/regulatory sequence is then propagated in E. coli HB101 and purified by centrifugation in cesium chloride-ethidium bromide gradients as described above. This plasmid is digested with the restriction endonuclease BamHI, phenol extracted, ethanol precipitated and resuspended in ligation buffer. The plasmid containing the HSV-1 BamHI N fragment (pBHVn) is digested with the restriction endonuclease BamHI, phenol extracted, ethanol precipitated and resuspended in TE. The BamHI digested pBHVn is incubated with 0.5 units CAP/microgram DNA for 30 minutes at 37° C/, phenol extracted, ethanol precipitated and resuspended in ligation buffer. The phosphatased pBHVn is ligated with BamHI digested pBHVtk2 at a ratio of 1:1 with 1.0 unit T4 DNA ligase/microliter reaction mixture at a concentration of 100 microgram DNA/ml for 2 hours, then overnight at 20 ug/ml. The ligated DNA is diluted 1:1 with TCM and used to transform calcium treated *E. coli* HB101. Ampicillin resistant, tetracycline sensitive colonies were identified. Selected colonies were tested for the presence of pBHVntk2 by preparation of quick plasmid DNA by the method of Birnboim and Doly. The plasmid was identified by the presence of the BamHI N fragment of HSV in a BamHI digest, as well as by restriction enzyme sites for EcoeI, KpnI, and PvuII known to be within the HSV BamHI N fragment. The plasmid was propagated in *E. coli* and purified by centrifugation in cesium chloride-ethidium bromide gradients as described above.

The eukaryotic expression vector is diagramatically represented in FIG. 1. FIG. 1 represents a pBR322 plasmid with PstI, EcorI, PvuII and BamHI restriction endonuclease sites with HSV-tk gene promoter/regulatory sequence inserted at the PvuII site and the HSV BAMHI N fragment inserted at the BamHI site. PvuII, BamHI, EcoRI, PstI, BglII, HincII and KpnI represent sites on the plasmid cleaved by the restriction endonuclease enzyme abbreviated by the respective symbol (IRL Press Limited, Falconberg Court, London W1V 5FG, V.K. pp 117).

Expression of Hepatitis B Virus Surface Antigen

The utility of the eukaryotic expression vector is demonstated by the ability to direct synthesis of HBsAg in baby hamster kidney cells (BHK) after insertion of HBsAg coding sequence into the expression vector and transformation of BHK cells, followed by infection of the BHK cells with HSV.

Preparation of HBsAg Coding Sequences

The HBsAg coding sequences are isolated by BamHI digestion of a recombinant plasmid containing the hepatitis B virus genome. The digested plasmid is electrophoresed on 5% polyacrylamide gels and the DNA visualized by ethidium-bromide staining and UV illumination. The portion of the gels containing the 1.3 kilobase pair (kbp) fragment is sliced out, placed in a small dialysis bag with 0.1 X TBE (50mMTris-borate pH 8.0, lmM EDTA) and electrophoresed in TBE until the ethidium-bromide stained DNA has migrated out of the gel slice and onto the dialyse bag. Electrophoretic polarity is reversed for 30 seconds, the DNA removed, concentrated by ethanol precipitation, and resuspended in ligation buffer.

Insertion of HBsAg Coding Sequences into Eukaryotic Expression Vector

The eukaryotic expression vector is digested with BglII, phenol extracted, ethanol precipitated and resuspended in TE. The digested DNA is incubated with CAP (0.5 units/ug DNA) at 37° C. for 30 minutes, phenol extracted and ethanol precipitated. The phosphatased eukaryotic expression vector is resuspended in ligation buffer and ligated to the 1.3 kbp HBsAg fragment at a ratio of 1:1 with T4 DNA ligase (1 unit/ul reaction mix) at a concentration of 100 ug DNA/ml for 16 hours at 16° C. The ligated DNA is diluted 1:1 with TCM and used to transform calcium treated *E. coli* HB101. Ampicillin resistant colonies are isolated and screened for the presence of the plasmid containing the 1.3 kbp HBsAg fragment by the method of Birnboim and Doly.

The restriction plasmid is identified by the presence of a unique XbaI (restriction endonuclease site) within a 3.3 kbp (kilobase pairs) PvuII fragment. This construction results in two types of inserts, one with the 5' end of the HBsAg coding sequences immediately adjacent to the tk promoter, and one in the opposite orientation. These plasmids were propagated in *E. coli* HB101 and purified by cesium chloride-ethidium bromide density gradient centrifugation as described above.

Expression of HBsAg with Virus

Ten micrograms of the plasmid with the HBsAg coding sequence adjacent the tk promoter are added to 1.0 ml HeBS (8 g/l NaCl, 0.37 g/l KCl, 0.25 g/l $Na_2HPO_4.2H_2O$, 1.0 g/l Dextrose, 5.0 g/l Hepes, pH 7.1), mixed well and 2.5 M $CaCl_2$ added to a final concentration of 0.125 M while a gentle stream of air is bubbled through the mixture during addition of $CaCl_2$ and for an additional 30 seconds. The DNA is allowed to precipitate for 30 minutes at room temperature and 0.5 ml is added to 25$cm^2$ dishes of baby hamster kidney cells (BHK). The cells are incubated with the DNA precipitate with gentle rocking at 37° C./ for 30 minutes and at 37° C./ without rocking for 30 minutes, 5 ml of EC-5 (Eagles minimal media with 5% calf serum) are added to each plate, and incubation continued for 3 hours at 37° C. Four hours after addition of the DNA, the culture medium is removed, cells are washed 1× with EC-5, and 1.0 ml of 25% dimethyl sulfoxide (DMSO) in Heps is added to each plate for 4 minutes at room temperature. The 25% DMSO is removed, dishes washed 2× with EC-5 and the cells incubated in EC-5 medium. The cells are infected with HSV (0.1lPFU/ml) 24 hours after addition of DNA and the infection allowed to proceed for 48 hours. HBsAg is isolated from the culture fluids by high speed centrifugation (3 hours at 100,000 ×g), resuspended as a 10× concentrate of the original volume and assayed with the Ausria II-125 HBsAg detection kit (Abbott Laboratories) as recommended by the manufacturer. HBsAg is routinely detected at levels ranging from $10^{4-5}$ molecules/cell.

EXAMPLE 2

Virus Independent Expression of Hepatitis B Virus Surface Antigen

The utility of the eukaryotic expression vector as a virus independent expression vector is demonstrated by the ability to direct synthesis of HBsAg in mouse-L thymidine kinase negative (Ltk−) cells after co-insertion into the cells of both the eukaryotic expression vector and the eukaryotic expression vector with the coding sequence for HBsAg inserted and subsequent selection of cells containing the thymide kinase positive (tk+) phenotype. In this instance the coding sequences of the expression vector serve as a selectable gene for isolation of those cells containing the tk+phenotype. Note that in this instance, any selection gene could be used in place of pBHVntk2, e.g., oncogenes, neomycin-kanamycin resitance. These cells express surface antigen in the absence of virus. The level of surface antigen synthesis can be amplified by infection with HSV.

Mouse Ltk— cells were propagated in Dulbecco's minimal medium supplemented with 10% fetal calf serum ; (DMEM-10) and containing 25 ug/ml bromodeoxyuridine (BUdR). Cells used for transformation were passaged once in DMEM without BUdR prior to insertion of DNA.

Expression of HBsAg

Five micrograms of the eukaryotic expression vector and 5 ug of that vector with the HBsAg coding sequence inserted are added to 1.0 ml HeBS, mixed well, and is $CaCl_2$ added to a final concentration of 0.125 M while a gentle stream of air is bubbled through the mixture during addition of $CaCl_2$ and for an additional 30 seconds. The DNA is allowed to precipitate for 30 minutes at room temperature and 0.5 ml added to $25cm^2$ dishes of Ltk— cells. The cells are incubated with the DNA precipitate for 1 hour at 37° C./ and 5 ml of DMEM containing 5% fetal calf serum (DMEM-5) are added and incubation is continued for 3 hours at 37° C. Four hours after addition of the DNA, the culture medium is removed and the cells are washed 2× with DMEM-×5. The transformed cells are incubated for an additional 24 hours in DMEM-5 at which time the growth medium is changed to selective HAT medium (DMEM-10 containing 15.0 ug/ml hypoxanthine, 0.2 ug/ml methotrexate, 5.0 ug/ml thymidine). Cells are in HAT medium for 2-3 weeks until tk+ clones are apparent. At this point a continuous cell line is established by trypinization of the clones and propagation in HAT medium, or single cell cloned lines obtained by limiting dilution of trypsinized cells in 96 well microtiter tissue culture trays. The cell lines are assayed for HBsAg as described in Example 1. HBsAg in synthesized in continuous cell lines at approximately $10^3$–$10^4$ molecules/cell/48 hours and can be amplified to approximately $10^4$–$10^5$ molecule/cell by infection with HSV. Levels of HbsAg from single cell cloned lines, expressing HBsAg, are approximately ten-fold higher than the parent continuous cell line.

What is claimed is:

1. A process for producing a mammalian cell line having cells containing extrachromosomal eukaryotic expression vectors, which process comprises the steps of:
   (a) inserting a herpes simplex virus (HSV) BamHI N fragment into a prokaryotic plasmid in a manner which does not disrupt the prokaryotic plasmid function to form a BamHI N fragment-containing plasmid;
   (b) adding a eukaryotic promoter and a gene to be expressed to the product of (a), said promoter and said gene to be expressed being operably linked to each other, and said promoter being located immediately 5' of said gene to be expressed;
   (c) introducing the plasmid of (b) into a mammalian cell; and
   (d) propagating said mammalian cell in the absence of HSV.

2. A process according to claim 1, wherein said mammalian cell is a baby hamster kidney cell.

3. A process according to claim 1, wherein said mammalian cell is a mouse Ltk-cell.

4. The process of claim 1 wherein said mammalian cell is propagated for at least thirty cell generations in he absence of HSV.

* * * * *